United States Patent [19]

Riley

[11] Patent Number: 5,094,842
[45] Date of Patent: Mar. 10, 1992

[54] ORAL COMPOSITIONS

[75] Inventor: Paul I. Riley, Bebington, Great Britain

[73] Assignee: Chesebrough-Pond's USA Co., Division of Conopco, Inc., Greenwich, Conn.

[21] Appl. No.: 592,426

[22] Filed: Oct. 4, 1990

[30] Foreign Application Priority Data

Oct. 6, 1989 [GB] United Kingdom ............... 8922594

[51] Int. Cl.$^5$ .................. A61K 7/16; A61K 7/18; A61K 7/24
[52] U.S. Cl. ........................... 424/52; 424/49; 424/57; 424/55
[58] Field of Search ...................... 424/49-58

[56] References Cited

U.S. PATENT DOCUMENTS

| | | |
|---|---|---|
| 3,538,230 | 11/1970 | Pader et al. ............ 424/50 |
| 4,022,880 | 5/1977 | Vinson et al. .......... 424/49 |
| 4,100,269 | 7/1978 | Pader .................... 424/49 |
| 4,144,323 | 3/1979 | Lamberti ............... 424/54 |
| 4,160,821 | 7/1979 | Sipos .................... 424/49 |
| 4,229,430 | 10/1980 | Fahim et al. .......... 424/642 |
| 4,259,316 | 3/1981 | Nakashima et al. ... 424/52 |
| 4,332,791 | 6/1982 | Raaf et al. ............. 424/52 |
| 4,335,102 | 6/1982 | Nakashima et al. ... 424/52 |
| 4,339,429 | 7/1982 | Raaf et al. ............. 424/49 |
| 4,339,432 | 7/1982 | Ritchey et al. ........ 424/54 |
| 4,363,794 | 12/1982 | Ochai et al. ........... 424/52 |
| 4,495,177 | 1/1985 | Taracatac et al. ..... 424/147 |
| 4,515,771 | 5/1985 | Fine ...................... 424/52 |
| 4,622,220 | 11/1986 | Frosch ................... 424/49 |
| 4,656,031 | 4/1987 | Lane et al. ............. 424/49 |
| 4,719,100 | 1/1988 | Frosch ................... 424/49 |
| 4,795,628 | 1/1989 | Afseth ................... 424/49 |
| 4,824,661 | 4/1989 | Wagner ................. 424/52 |
| 4,970,064 | 11/1990 | Adam et al. ........... 424/52 |
| 4,997,640 | 3/1991 | Bird et al. ............. 424/52 |
| 5,004,597 | 4/1991 | Majetl et al. .......... 424/52 |

FOREIGN PATENT DOCUMENTS

| | | |
|---|---|---|
| 0321282 | 6/1989 | European Pat. Off. . |
| 2406437 | 5/1979 | France . |
| 2007974 | 5/1979 | United Kingdom . |
| 2080681 | 2/1982 | United Kingdom . |
| 2167956 | 6/1986 | United Kingdom . |

OTHER PUBLICATIONS

Harry's Cosmeticology, 7th Edition (1982), pp. 609-617.

*Primary Examiner*—Shep K. Rose
*Attorney, Agent, or Firm*—Milton L. Honig

[57] ABSTRACT

The invention relates to oral compositions such as toothpastes which contain Vitamin C and a copper compound such as copper sulphate. The tendency of these compositons to discolor, particularly if they also contain a zinc compound such as zinc citrate, can be reduced by the inclusion in the compositions of a stannous compound such as stannous pyrophosphate.

6 Claims, No Drawings

ORAL COMPOSITIONS

The present invention relates to oral compositions such as mouthwashes, dentifrices, toothpastes, teeth cleaning powders and tablets, gels for the treatment of teeth etc. More particularly, it relates to oral compositions which contain as essential ingredients Vitamin C or a derivative thereof, such as a salt or an ester, and a copper compound which is capable of releasing copper ions such as water soluble copper (II) salts.

Such oral compositions have been described and claimed in our European patent application 0 321,282, published on 21 June 1989. Although these compositions are relatively stable, effective products for the control of gingivitis and/or periodontitis, they show a tendency to discolour, mainly at the surface of the product, not only when exposed to air upon extrusion of the toothpaste from the container, but also during storage of the toothpaste in a closed container at various temperatures. In our above EP 0 321,282 it is recommended to minimize the slight discolouration of an extruded toothpaste ribbon by formulating the toothpaste to give a lower pH of from about 4 to about 5.

We have now surprisingly found, that such discolouration can also be prevented or reduced to a significant degree by inclusion in these oral compositions of a stannous compound, capable of releasing stannous ions in the compositions. Not only is the discolouration of the toothpaste when exposed to air upon extrusion from the container significantly reduced, but also the discolouration of the toothpaste which may occur in the container during storage of the toothpaste in the container.

Consequently, the present invention in its broadest aspect relates to an oral composition comprising vitamin C or a salt or an ester thereof, and a copper compound, capable of releasing copper ions, said composition having a reduced tendency to discolour upon storage and upon exposure to air, characterised in that it further contains an effective amount of a stannous compound, capable of releasing stannous ions.

We have further found, that the present invention is of particular benefit when the oral composition also contains a zinc compound. Compositions, which contain Vitamin C, a copper compound and a zinc compound have a greater tendency to discolour, and by inclusion of the stannous compound said discolouration is also significantly reduced.

The stannous compound, useful in the present invention, can be any inorganic and/or organic stannous compound, capable of releasing stannous ions. Typical examples of suitable stannous compounds are stannous fluoride, stannous chloride, stannous chloride fluoride, stannous acetate, sodium stannous fluoride, potassium stannous fluoride, stannous hexafluorozirconate, stannous sulfate, stannous tartrate, stannous gluconate, stannous pyrophosphate, stannous metaphosphate, stannous oxalate, stannous phosphate etc.

Stannous fluoride, and particularly stannous pyrophosphate are the preferred stannous salts. Mixtures of various stannous salts may also be used. A preferred mixture is the mixture of stannous fluoride and stannous pyrophosphate. The stannous compound is generally used in an amount of 0.01-10% by weight of the composition, usually 0.02-5% by weight and preferably 0.1-3% by weight.

The oral compositions of the present invention containing Vitamin C, or a salt or ester thereof, a copper compound capable of releasing copper ions and other ingredients are substantially of the same type as more fully described in our aforesaid EP 0 321,282 and the full disclosure thereof is therefore hereby incorporated by way of Reference.

Thus, the Vitamin C, or salt or ester thereof, may be present in the product of the invention in an amount of from about 0.05% to about 5%, preferably about 0.5% to about 5% by weight of the product. A mixture of two or more of ascorbic acid, ascorbic salt and ascorbic acid ester may of course be used.

Any physiologically acceptable salt of ascorbic acid may be used. Various alkali metal and alkaline earth metal salts are suitable. Other suitable salts are the ammonium salt and those derived from monoethanolamine, diethanolamine, and amino acids such as arginine and lysine.

Suitable ascorbic acid esters are those in which one or more hydroxy groups in the 2-, 3,-, 5- and/or 6-positions are fatty acid ester, sulphate or phosphate. Examples are ascorbic acid-2-acetate, ascorbic acid-2-sulphate, ascorbic acid-2-phosphate, ascorbic acid-2-palmitate.

The copper compound is preferably incorporated in the product of the invention in the form of a water-soluble copper salt to provide copper ions in the aqueous liquid medium of the toothpaste. Any suitable physiologically acceptable salt may be used. Examples of suitable copper salts are copper sulphate, copper halides and pseudohalides, copper nitrate, copper salts of carboxylic acids in the homologous series formic acid to decanoic acid, copper salts of polybasic acids in the series oxalic acid to suberic acid, and copper salts of hydroxycarboxylic acids including glycolic acid, lactic acid, tartaric acid, malic acid and citric acid.

The copper compound may also be included in the toothpaste of the invention in the form of a copper compound precipitated on a solid or colloidal support such as silica, a clay (e.g. montmorillonite) or upon a biopolymer or synthetic polymer. Copper compounds which are substantially insoluble but which nevertheless release sufficient copper ions, such as copper hydrotalcite, may also be used.

The amount of copper compound, calculated as copper, which is included in compositions according to the present invention ranges from about 1 ppm to 1000 ppm, preferably 10 to 200 ppm, more preferably 30 to 100 ppm.

Examples of zinc salts suitable for use in the oral composition of the invention are disclosed in U.S. Pat. Nos. 4,100,269, U.S. Pat. No. 4,022,880, 4,160,821 and U.S. Pat. No. 4,656,031. These include by way of example, zinc citrate, zinc chloride and zinc sulphate. Examples of other zinc salts that have been proposed are zinc carboxymethyloxysuccinate (U.S. Pat. No. 4,144,323), zinc glycinate (U.S. Pat. No. 4,339,432), and zinc aspartate (U.S. Pat. No. 4,622,220). Zinc citrate is the preferred zinc salt.

The amount of the zinc salt used in the ora composition of the invention may be from about 0.05% to about 1.5%, preferably from about 0.1% to about 0.7%, calculated as zinc.

The balance of the oral composition consists of an orally acceptable medium, the nature of which depends upon the final application form.

The oral composition of the invention is preferably in the form of a toothpaste, by which term we include products sometimes referred to as dental creams or gels. Toothpaste usually comprise a suspension of a particulate solid abrasive cleaning agent in a thickened aqueous humectant liquid In the oral composition of this invention various of the known abrasive cleaning agents can be used but silica abrasives are preferred. A number of forms of silica are already known in the art as being suitable for dentifrice use including silica xerogels, precipitated silicas and crystalline silicas Such silicas are referred to in U.S. Pat. No. 3,538,230 and GB-A-2,167,856. Other compatible abrasives include water-insoluble sodium metaphosphate, alumina, calcium pyrophosphate and plastics materials. Alumina abrasives include the hydrated aluminas A conventional level of abrasive ranging from 5 to 75% by weight of the toothpaste may be used. As is well know, use of various silica abrasives permits the toothpaste to be formulated in the form of a transparent or translucent gel product.

Humectants which may be used include glycerol, sorbitol syrup, polyethylene glycol, lactitol, xylitol or hydrogenated corn syrup. The total amount of humectant present will generally range from 10% to 85% by weight of the toothpaste, more usually 20% to 60%.

The remaining liquid phase of toothpaste according to the invention mainly comprises water which will usually amount from about 5% to about 45% by weight of the toothpaste. The amount of water in the toothpaste, including any present in the humectant, will generally be in the range about 5% to about 60%, such as from about 10% to about 55% by weight of the toothpaste.

Numerous binding or thickening agents have been indicated for use in toothpastes, preferred ones being hydroxymethylcellulose, sodium carboxymethylcellulose and xanthan gum. Others include natural gum binders such as gum tragacanth, gum karaya and gum arabic, Irish moss alginates and carrageenans. Silica thickening agents include the silica aerogels and various precipitated silicas. Mixtures of binders and thickening agents may be used. The amount of binder and thickening agent included in a toothpaste is generally between 0.1 to 10% by weight Toothpastes generally also comprise a surfactant. Commonly used is sodium lauryl sulphate but others are also known to be suitable. The amount of surfactant is usually within the range 0.5 to 5% by weight of the composition.

A variety of other known toothpaste ingredients may also be included in toothpastes formulated in accordance with the present invention. Such ingredients include an anticaries ingredient such as casein and casein digests, hydroxyapatites, trimetaphosphates sodium fluoride or sodium monofluorophosphate or other effective fluorinecontaining compound; an additional anti-plaque agent such as an antimicrobial compound for example chlorhexidine or 2,4,4'-trichloro-2'-hydroxy-diphenyl ether; sweetening agent such as saccharin; an opacifying agent such as titanum dioxide; a preservative such as formalin; a flavouring agent such as peppermint oil or spearmint oil; a colouring agent; or pH controlling agent such as an acid, base or buffer, for example benzoic acid, to give a pH of from about 4 to about 8, preferably about 5 to about 7; anti-calculus agents such as alkalimetal-pyrophosphates; polymers such as polyvinylmethylether-maleic anhydride copolymers and so on.

Preferred oral compositions of this invention contain 500–5000 ppm F, preferably 1000–2500 ppm F, as ionic fluoride or monofluorophosphate.

For a further discussion of the formulation of toothpastes reference is made to Harry's Cosmeticology, Seventh Edition 1982, Edited by J.B. Wilkinson and R.J. Moore, pages 609 to 617.

The following Example further illustrates the invention:

|  | A | B | C | D |
|---|---|---|---|---|
| Silica xerogel | 10.0 | 10.0 | 10.0 | 10.0 |
| Silica aerogel | 8.0 | 8.0 | 8.0 | 8.0 |
| Sorbitol syrup (70%) | 40.5 | 40.0 | 40.0 | 40.0 |
| Titanium dioxide | 1.0 | 1.0 | 1.0 | 1.0 |
| Xanthan gum | 1.0 | 1.0 | 1.0 | 1.0 |
| Sodium laurylsulphate | 1.5 | 1.5 | 1.5 | 1.5 |
| Saccharin | 0.2 | 0.2 | 0.2 | 0.2 |
| Sodium monofluorophosphate | 0.82 | 0.82 | 0.82 | — |
| Copper (II) sulphate pentahydrate | 0.019 | 0.019 | 0.019 | 0.019 |
| Vitamin C | 2.0 | 2.0 | 2.0 | 2.0 |
| Flavour | 1.0 | 1.0 | 1.0 | 1.0 |
| Colouring agent | 0.0072 | 0.0072 | 0.0072 | 0.0072 |
| Stannous flouride | — | — | — | 0.4 |
| Stannous pyrophosphate | — | — | 0.4 | — |
| Zinc citrate trihydrate | — | 0.5 | 0.5 | 0.5 |
| Water | to 100.0 | to 100.0 | to 100.0 | to 100.0 |

These pastes were made with a green colour, and a similar series was made without the green colour to leave them white. The pastes were tubed on the same day of manufacture. They were subsequently stored at controlled temperatures of 6°, 20° and 37° C. Visual observations for discolouration were made after three and six month's storage. Water-extractable vitamin C was also determined, by titration with dichlorophenol indophenol, and with iondine. The following results were obtained.

|  | A | B | C | D |
|---|---|---|---|---|
| Discolouration after 3 months at |  |  |  |  |
| 6° C. | + | ++ | — | — |
| 20° C. | + | ++ | — | — |
| 37° C. | ++ | +++ | + | + |
| After 6 months at |  |  |  |  |
| 6° C. | + | ++ | — | — |
| 20° C. | + | ++ | —/+ | — |
| 37° C. | ++ | +++ | + | ++ |

The number of plus signs corresponds with an increasing degree of brown discolouration ranging from very slight discolouration (+) to very severe darkish discolouration (+++++); a minus sign indicates no substantial brown discolouration.

The residual water-extractable Vitamin C levels (in %) after six months' storage were:

|  | A | B | C | D |
|---|---|---|---|---|
| at 6° C. | 1.94 | 1.97 | 2.0 | 1.9 |
| at 20° C. | 1.82 | 1.79 | 1.8 | 1.8 |
| at 37° C. | 1.53 | 1.40 | 0.8 | <0.1 |

I claim:

1. An oral composition in the form of a mouthwash dentifrice, toothpaste, teeth-cleaning powder, teeth-cleaning tablet or teeth-cleaning gel, said composition having a reduced tendency to discolor upon storage and upon exposure to air, said composition having a pH from about 4 to about 8 and comprising in an orally acceptable medium:
  (i) from 0.05 to 5% by weight of an ascorbic substance selected from the group consisting of ascorbic acid, physiologically acceptable alkali metal, alkaline earth metal, ammonium, alkanol ammonium and amino acid salts of ascorbic acid, and ascorbic acid esters in which at least one hydroxy group has been converted to a fatty acid ester, sulphate or phosphate;
  (ii) from 1 ppm to 1000 ppm, calculated as copper, of a copper-ion releasing copper compound selected from the group consisting of copper sulphate, copper halides and phseudohalides, copper nitrate, copper salts of carboxylic acids in the homologous series formic acid to decanoic acid, copper salts of polybasic acids in the series oxalic acid to suberic acid, copper salts of hydroxycarboxylic acids selected from glycolic acid, lactic acid, tartaric acid, malic acid and citric acid, copper precipitated on a solid or colloidal support selected from silica, clay, biopolymer and synthetic polymer, and copper hydrotalcite; and
  (iii) from 0.01 to 10% by weight of a stannous-ion releasing stannous compound selected from the group consisting of stannous fluoride, stannous chloride, stannous chloride fluoride, stannous fluoride, stannous hexafluorozirconate, stannous sulfate, stannous tartrate, stannous gluconate, stannous pyrophosphate, stannous metaphosphate, stannous oxalate and stannous phosphate.

2. An oral composition according to claim 1, comprising from 0.1 to 3% by weight of the stannous compound.

3. An oral composition according to claim 1, wherein the stannous compound is selected from the group consisting of stannous fluoride, stannous pyrophosphate and mixtures thereof.

4. An oral composition according to claim 1, further containing from 0.05% to 1.5% by weight, calculated as zinc, of a zinc salt selected from the group consisting of zinc citrate, zinc chloride, zinc sulphate, zinc carboxymethyloxysuccinate, zinc glycinate and zinc aspartate.

5. An oral composition according to claim 4, wherein the zinc salt is zinc citrate.

6. A method for reducing discoloration of an oral composition upon storage and upon xposure to air, said method comprising incorporating from 0.01 to 10% by weight of a stannous-ion releasing stannous compound selected from the group consisting of stannous fluoride, stannous chloride, stannous chloride fluoride, stannous fluoride, stannous hexafluorozirconate, stannous sulfate, stannous tartrate, stannous gluconate, stannous pyrophosphate, stannous metaphosphate, stannous oxalate andstannous phosphate, into an oral composition which is a mouthwash, dentifrice, toothpaste teeth-cleaning powder, teeth-cleaning tablet or teeth-cleaning gel, said composition having a pH from about 4 to about 8 and comprising in an orally acceptable medium:
  (i) from 0.05 to 5% by weight of an ascorbic substance selected from the group consisting of ascorbic acid, physiologically acceptable alkali metal, alkaline earth metal, ammonium, alkanol ammonium and amino acid salts of ascorbic acid, and ascorbic acid esters in which at least one hydroxy group has been converted to a fatty acid ester, sulphate or phosphate; and
  (ii) from 1 ppm to 1000 ppm, calculated as copper, of a copper-ion releasing copper compound selected from the group consisting of copper sulphate, copper halides and pseudohalides, copper nitrate, copper salts of carboxylic acids in the homologous series formic acid to decanoic acid, copper salts of polybasic acids in the series oxalic acid to suberic acid, copper salts of hydroxycarboxylic acids selected from glycolic acid, lactic acid, tartaric acid, malic acid and citric acid, copper precipitated on a solid or colloidal support selected from silica, clay, biopolymer and synthetic polymer, and copper hydrotalcite.

* * * * *